US00PP34834P2

(12) United States Plant Patent
Post

(10) Patent No.: US PP34,834 P2
(45) Date of Patent: Dec. 13, 2022

(54) ***CHRYSANTHEMUM* PLANT NAMED 'DLFOLGA2'**

(50) Latin Name: ***Chrysanthemum* X *morifolium***
Varietal Denomination: DLFOLGA2

(71) Applicant: Arie Gerard Post, Delft (NL)

(72) Inventor: Arie Gerard Post, Delft (NL)

(73) Assignee: DELIFOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/833,831

(22) Filed: Jun. 6, 2022

Related U.S. Application Data

(60) Provisional application No. 63/197,948, filed on Jun. 7, 2021.

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./289, 295
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Chrysanthemum* plant named 'DLFOLGA2', characterized by its upright plant habit; uniform growth habit; vigorous growth habit and rapid growth rate; durable and robust dark green-colored leaves; strong upright flowering stems; decorative-type inflorescences with bright yellow-colored ray florets; relative tolerance to high and low production temperatures; and good postproduction longevity.

2 Drawing Sheets

Figure 1:
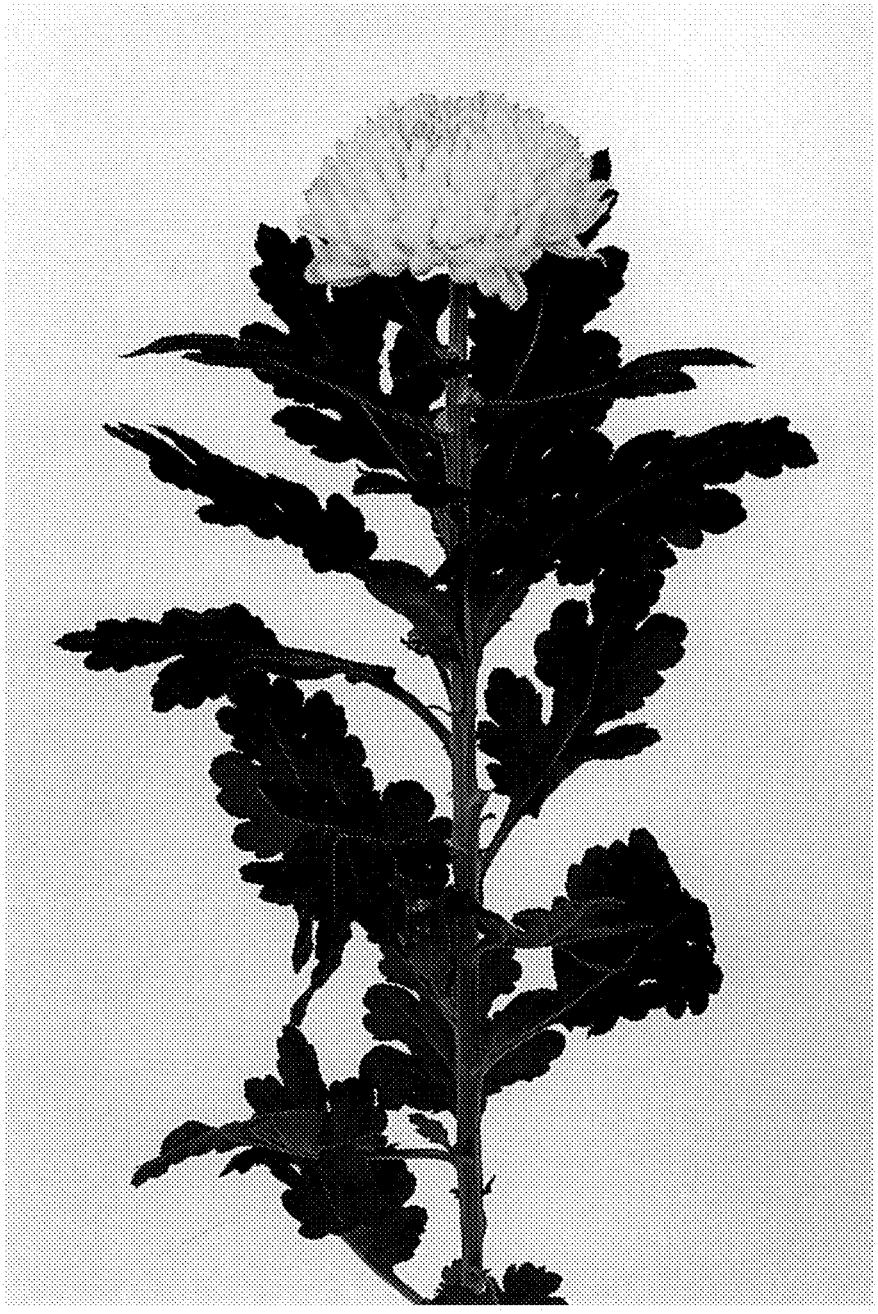

Botanical designation: *Chrysanthemum* X *morifolium*.
Cultivar denomination: 'DLFOLGA2'.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Jul. 6, 2021, application number A212799. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFOLGA2'.

The new *Chrysanthemum* plant is a product of a planned breeding program conducted by the Inventor in Maasdijk, The Netherlands. The objective of the breeding program is to create new cut flower *Chrysanthemum* plants with unique and attractive inflorescences.

The new *Chrysanthemum* plant originated from a cross-pollination in March, 2013 of a proprietary selection of *Chrysanthemum* x *morifolium* identified as code number KR 8722, not patented, as the female, or seed, parent with a proprietary selection of *Chrysanthemum* x *morifolium* identified as code number KR 2011.1429-1, not patented, as the male, or pollen, parent. The new *Chrysanthemum* plant was discovered and selected as a single flowering plant from within the progeny of the stated cross-pollination in a controlled greenhouse environment in Maasdijk, The Netherlands in December, 2013.

Asexual reproduction of the new *Chrysanthemum* plant by vegetative terminal cuttings in a controlled greenhouse environment in Maasdijk, The Netherlands since December, 2013 has shown that the unique features of this new *Chrysanthemum* plant are stable and reproduced true to type in successive generations of asexual reproduction.

SUMMARY OF THE INVENTION

The following traits have been repeatedly observed and are determined to be the unique characteristics of 'DLFOLGA2'. These characteristics in combination distinguish 'DLFOLGA2' as a new and distinct *Chrysanthemum* plant:

1. Upright plant habit; uniform growth habit.
2. Vigorous growth habit and rapid growth rate.
3. Durable and robust dark green-colored leaves.
4. Strong upright flowering stems.
5. Decorative-type inflorescences with bright yellow-colored ray florets.

6. Relatively tolerant to high and low production temperatures.
7. Good postproduction longevity.

Plants of the new *Chrysanthemum* differ primarily from plants of the female parent selection in the following characteristics:

1. Leaf sinuses of plants of the new *Chrysanthemum* are convergent whereas leaf sinuses of plants of the female parent selection are parallel.
2. Ray floret apices of plants of the new *Chrysanthemum* are broadly acute with occasional indentations whereas ray floret apices of plants of the female parent selection are mamillate.

Plants of the new *Chrysanthemum* differ primarily from plants of the male parent selection in the following characteristics:

1. Leaves of plants of the new *Chrysanthemum* have glossier upper leaf surfaces than leaves of plants of the male parent selection.
2. Ray floret apices of plants of the new *Chrysanthemum* are broadly acute with occasional indentations whereas ray floret apices of plants of the male parent selection are mamillate.

Plants of the new *Chrysanthemum* can be compared to plants of *Chrysanthemum* X *morifolium* 'DLFASTR2', not patented. In side-by-side comparisons, plants of the new *Chrysanthemum* differ primarily from plants of 'DLFASTR2' in leaf size and color as plants of the new *Chrysanthemum* have shorter and darker green-colored leaves than plants of 'DLFASTR2'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a side perspective view of a typical flowering stem of 'DLFOLGA2' grown as a disbud-type cut flower.

Figure 2:
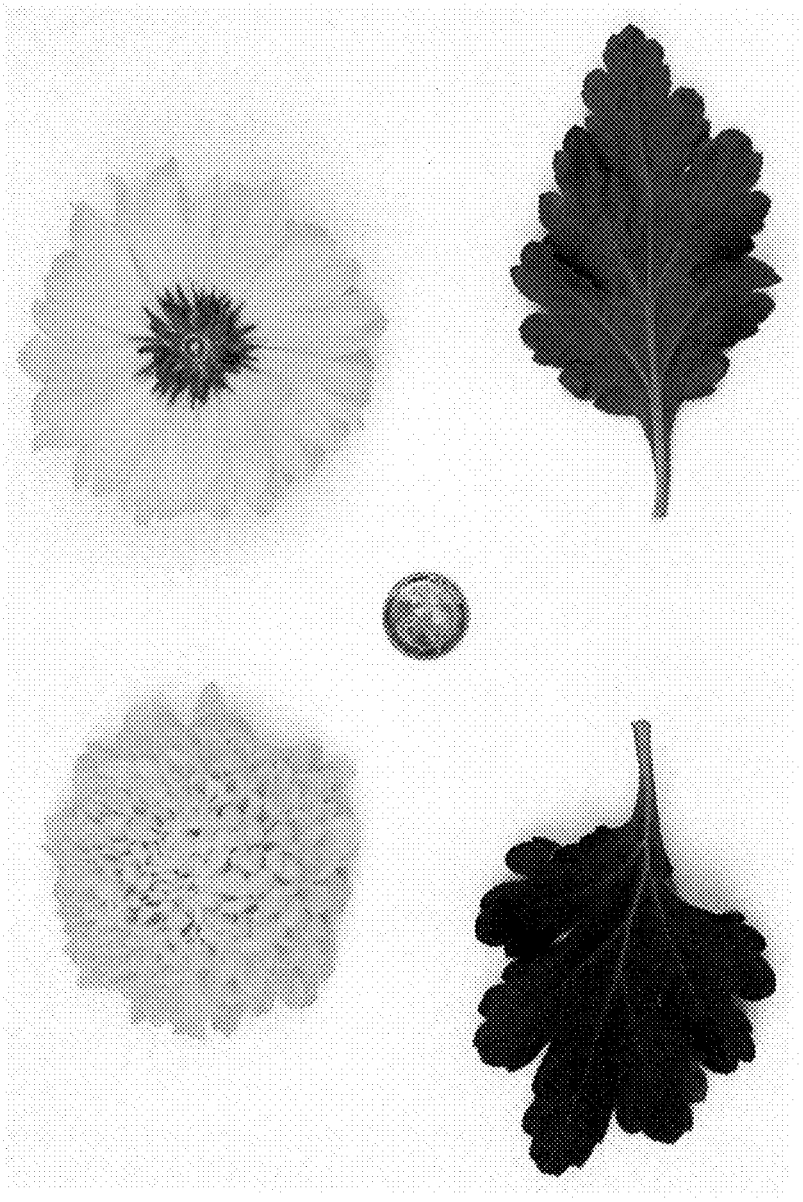

The photograph on the second sheet (FIG. 2) is a close-up view of upper (left) and lower (right) surfaces of typical inflorescences and typical leaves of 'DLFOLGA2'.

DETAILED BOTANICAL DESCRIPTION

The aforementioned photographs and following observations and measurements describe plants grown during the early spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 7 klux. Plants were grown as single-stem disbud-type plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFOLGA2'.

Parentage:

*Female, or seed, parent*.—Proprietary selection of *Chrysanthemum* x *morifolium* identified as code number KR 8722, not patented.

*Male, or pollen, parent*.—Proprietary selection of *Chrysanthemum* x *morifolium* identified as code number KR 2011.1429-1, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem disbud-type; upright plant habit; vigorous growth habit and rapid growth rate.

*Plant height, soil level to top of foliar plane*.—About 74.2 cm.

*Plant height, soil level to top of inflorescence plane*.—About 76.4 cm.

*Plant (spray) diameter*.—About 23.2 cm.

*Flowering stem length*.—About 69.1 cm.

*Flowering stem diameter*.—About 7 mm.

*Flowering stem internode length*.—About 1.7 cm.

*Flowering stem strength*.—Strong.

*Flowering stem aspect*.—Erect.

*Flowering stem texture and luster*.—Densely pubescent; slightly glossy.

*Flowering stem color, developing*.—Close to 144B to 144C.

*Flowering stem color, developed*.—Close to 138B; at the ridges, close to 148C.

*Leaf description*.—Arrangement: Alternate; simple. Length: About 11.2 cm. Width: About 7.1 cm. Shape, in overall outline: Broadly ovate. Apex: Minutely abruptly acute. Base: Attenuate. Margin: Palmately lobed, coarsely crenate to dentate; sinuses convergent and medium in depth; slightly undulate. Texture and luster, upper surface: Moderately to densely pubescent, not rugose; moderately velvety; slightly glossy. Texture and luster, lower surface: Densely pubescent, not rugose; slightly velvety; slightly glossy. Venation pattern: Pinnate. Color: Developing leaves, upper surface: Close to 137A. Developing leaves, lower surface: Close to 147B. Fully developed leaves, upper surface: Darker than a blend of 139A and 147A; venation, close to 146B. Fully developed leaves, lower surface: Close to 147B; venation, close to 146B. Petioles: Length: About 2.8 cm. Diameter: About 3.5 mm by 5 mm. Strength: Moderately strong. Texture and luster, upper and lower surfaces: Densely pubescent; slightly glossy.

Color, upper surface: Close to 146B; edges, close to 139A. Color, lower surface: Close to 146D; edges, close to 147B. Stipules: Quantity and appearance: If present, two leafy stipules, opposite, at the petiole attachment to the stem. Length: About 6 mm. Width: About 3 mm. Shape: Elliptic; apex, short apiculate; base, broadly cuneate; margins, entire. Texture and luster, upper and lower surfaces: Densely pubescent; slightly glossy. Color, upper surface: Darker than a blend of 139A and 147A. Color, lower surface: Close to 147B.

Inflorescence description:

*Appearance*.—Decorative-type inflorescence form with oblanceolate-shaped ray florets and tubular disc florets; inflorescences, rotate and flattened hemispherical in overall shape; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plants flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 50 days later when grown as a disbud-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a disbud-type, only the terminal inflorescence is allowed to develop.

*Inflorescence size*.—Diameter: About 10.7 cm. Depth (height): About 6.5 cm. Disc diameter: About 2.2 cm; inconspicuous.

*Receptacles*.—Height: About 5 mm. Diameter: About 1.5 cm. Shape: Broad flattened hemispherical. Color: Close to 145C.

*Inflorescence buds*.—Height: About 9 mm. Diameter: About 1.7 cm. Shape: Flattened globular. Texture and luster: Moderately pubescent; slightly glossy. Color: Developing involucral bracts, close to 137B and 144D; developing ray florets, close to 154C; developing disc florets, close to 144B.

*Ray florets*.—Quantity and arrangement: About 240 arranged in about seven whorls. Length: About 4.5 cm, varying between 1.6 cm and 5.8 cm. Width: About 1.15 cm, varying between 0.2 cm and 1.7 cm. Shape: Oblanceolate; strongly concave. Apex: Broadly acute with occasional indentations. Base: Narrowly cuneate. Margin: Entire; not undulate. Aspect: About 30° from vertical, varying from −20 ° to 80 ° from vertical. Texture and luster, upper surface: Smooth, glabrous; slightly velvety; matte. Texture and luster, lower surface: Smooth, glabrous; slightly glossy. Color: When opening, upper surface: Close to 6A. When opening, lower surface: Close to 7C. Fully opened, upper surface: Close to 6A to 6B; venation, close to 6A to 6B; color does not change with subsequent development. Fully opened, lower surface: Close to 5A to 5B; venation, close to 5A to 5B; color does not change with subsequent development.

*Disc florets*.—Quantity and arrangement: About 320 randomly arranged at the center of the receptacle. Length: About 6 mm. Diameter: About 2 mm. Shape: Tubular; proximally, 87.5% of the floret is fused. Apex: Acute. Margin, free-part: Entire. Texture and luster, inner and outer surfaces: Smooth, glabrous; glossy. Color, when opening, inner and outer surfaces: Apex: Close to 151D. Mid-section and towards the base: Close to 145C. Color, fully opened, inner and outer surfaces: Apex: Close to 12A. Mid-section and towards the base: Close to 145C.

*Involucral bracts*.—Quantity and arrangement: About 50 arranged in about three whorls. Length: About 1.4 cm. Width: About 5 mm. Shape: Narrowly oblong to narrowly ovate. Apex: Bluntly acute. Base: Cuneate. Margin: Entire. Texture and luster, upper surface: Smooth, glabrous; glossy. Texture and luster, lower surface: Moderately pubescent; slightly glossy. Color, upper surface: Close to 146B; lateral margins, translucent and close to 157D and apical margins slightly tinged with close to N199A. Color, lower surface: Close to NN137D; lateral margins, translucent and close to 157D and apical margins slightly tinged with close to N199A.

*Peduncles*.—Length: About 4.5 cm. Diameter: About 6 mm. Strength: Strong. Aspect: Upright. Texture and luster: Densely pubescent; slightly glossy. Color: Close to 138B; at the ridges, close to 148C to 148D.

*Reproductive organs*.—Androecium: Present on disc florets only. Quantity: About five per floret. Filament length: About 2 mm. Filament color: Close to 157D. Anther size: About 0.5 mm by 2 mm. Anther shape: Narrowly oblong. Anther color: Close to 164A. Pollen amount: Scarce. Pollen color: Close to 13A. Gynoecium: Present on both ray and disc florets. Quantity: One per floret. Pistil length: About 8 mm. Style length: About 7 mm. Style color: Close to 2B. Stigma diameter: About 1 mm. Stigma shape: Cleft, decurrent. Stigma color: Close to 153D. Ovary color: Close to 145D.

*Seeds and fruits*.—To date, seed and fruit development have not been observed on plants of the new *Chrysanthemum*.

Pathogen & pest resistance: Plants of the new *Chrysanthemum* have been observed to be resistant to *Verticilium* Wilt (*Verticilium dahliae*) and Western Flower Thrips (*Frankliniella occidentalis*). To date, plants of the new *Chrysanthemum* have not been observed to be resistant to other pathogens and pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFOLGA2' as illustrated and described.

* * * * *